United States Patent [19]
Lebaut et al.

[11] Patent Number: 6,008,231
[45] Date of Patent: Dec. 28, 1999

[54] N-SUBSTITUTED INDOLE-3 GLYOXYLAMIDES HAVING ANTI-ASTHMATIC ANTIALLERGIC AND IMMUNOSUPPRESSANT/IMMUNO-MODULATING ACTION

[75] Inventors: Guillaume Lebaut, Saint Sebastien/Loire; Cécilia Menciu, Nantes, both of France; Bernhard Kutscher, Maintal, Germany; Peter Emig, Bruchköbel, Germany; Stefan Szelenyi, Schwaig, Germany; Kay Brune, Marloffstein/Rathsberg, Germany

[73] Assignee: ASTA Medica Aktiengesellschgt, Germany

[21] Appl. No.: 08/925,326

[22] Filed: Sep. 8, 1997

[30] Foreign Application Priority Data

Sep. 6, 1996 [DE] Germany ............ 196 36 150

[51] Int. Cl.$^6$ ............ A61K 31/40; C07D 209/04; C07D 209/12; C07D 401/06
[52] U.S. Cl. ............ 514/314; 514/339; 514/419; 546/168; 546/278.1; 548/491; 548/493
[58] Field of Search ............ 514/339, 314, 514/419; 546/278.1, 168; 548/491, 493

[56] References Cited

U.S. PATENT DOCUMENTS 3,135,794  6/1964  Archer ............ 260/562
3,801,594  4/1974  Poletto et al. ............ 260/326.15

FOREIGN PATENT DOCUMENTS 675110  4/1995  European Pat. Off. .

OTHER PUBLICATIONS

Glamkowski et al., "Synthesis of 3–(4–Acylaminopiperazin–1–ylalkyl)indoles as Potential Antihypertensive Agents," J. Med. Chem., vol. 20, No. 11, pp. 148–152, 1977.

Archibald et al., "1,4–Bis(2–indol–3–ylethyl)piperazines," J. Med. Chem., vol. 17, No. 7, pp. 745–747, 1974.

Domschke et al., "Notiz zur Darstellung einiger [1–Benzyl–2–methyl–5–methoxy–indolyl–(3)]–glyoxylsaureamide," vol. 94, pp. 2353–2355, 1961.

Lipp et al., "Notiz uber einige Derivate der [5–Benzyloxy–indolyl–(3)]–glyoxylsaure," Chem. Ber., vol. 91, pp. 242–243, 1957.

Chem. Abstr. 92: 128647h. CXIV. Eryshev et al., "Synthesis of anilides of indolylalkanoic acids," vol. 92, p. 673, 1980.

Chem. Abstr. 120:125105r Evans et al., "Probing the 5–HT3 receptor site using novel indole–3–glyoxylic acid derivatves," vol. 120, p. 123, 1994.

Chem. Abstr. 115007v American Home Products, "Therapeutic bis(indolyl) compounds," vol. 70, p. 15007, 1969.

Chem. Abstr. 37598x Podwinski, "Synthesis of some 5–benzyloxyindole–3–glyoxylic acid amides," vol. 70, p. 327, 1969.

Chem. Abstr. 9293 Sterling Drug Inc., "Indolylpiperazines," vol. 60, 1964.

Chem. Abstr. 3871 P'eng et al., "Synthesis of derivatives of 5,6–disubstituted 3–(Beta–aminoethyl)–indole," vol. 65, 1966.

Chem. Abstr. 53968m Bertaccini et al., "Synthesis and Pharmacological activity of some 5–methoxyindole derivatives occurring in nature," vol. 67, p. 5069, 1967.

Chem. Abstr. 87491p Brewster et al., "Antihypertensive 1,4–bis(2–indol–3–ylethyl)piperazines," vol. 79, p. 27, 1973.

Chem. Abstr. 86: 106379w Alvarez et al., "3–(2–Aminoethyl)indole derivatives," vol. 86, p. 491, 1977.

Evans et al., "Probing the 5–HT3 receptor site using novel indole–3–glyoxylic acid derivatives," Med. Chem. Res., 3(5–6), pp. 386–406, 1993.

Primary Examiner—Johann Richter
Assistant Examiner—Jane C. Oswecki
Attorney, Agent, or Firm—Pillsbury Madison & Sutro

[57] ABSTRACT

The invention relates to novel N-substituted indole-3-glyoxylamides, to processes for their preparation and to their pharmaceutical use. The compounds have antiasthmatic, antiallergic and immuno-suppressant/immunomodulating actions.

11 Claims, No Drawings

N-SUBSTITUTED INDOLE-3 GLYOXYLAMIDES HAVING ANTI-ASTHMATIC ANTIALLERGIC AND IMMUNOSUPPRESSANT/IMMUNO-MODULATING ACTION

BACKGROUND OF THE INVENTION

1. Field of the Invention

The invention relates to novel N-substituted indole-3-glyoxylamides, processes for their preparation and pharmaceutical uses. The compounds have antiasthmatic, antiallergic and immunosuppressant/immunomodulating properties.

2. Background Information

Indole-3-glyoxylamides have various uses as pharmacodynamically active compounds and as synthesis components in the pharmaceutical chemistry.

The Patent Application NL 6502481 describes compounds which have an antiinflammatory and antipyretic profile of action and analgesic activity.

The British Patent GB 1 028 812 mentions derivatives of indolyl-3-glyoxylic acid and its amides as compounds having analgesic, anticonvulsant and β-adrenergic activity.

G. Domschke et al. (Ber. 94, 2353 (1961)) describe 3-indolylglyoxylamides which are not characterized pharmacologically.

E. Walton et al. in J. Med. Chem. 11,1252 (1968) report on indolyl-3-glyoxylic acid derivatives which have an inhibitory activity on glycerophosphate dehydrogenase and lactate dehydrogenase.

Euoropean Patent Specification EP 0 675 110 A1 describes 1H-indole-3-glyoxylamides which are profiled as sPLA2 inhibitors and are used in the treatment of septic shock, in pancreatitis, and in the treatment of allergic rhinitis and rheumatoid arthritis.

SUMMARY OF THE INVENTION

The aim of the present invention is to make available novel compounds from the indolyl-3-glyoxylic acid series, which have antiasthmatic and immunomodulating action.

The chemical processes for the preparation of these compounds and pharmaceutical processes for the conversion of the novel compounds into medicaments and their preparation forms are furthermore described.

The subject matter of the invention comprises compounds of the general formula I,

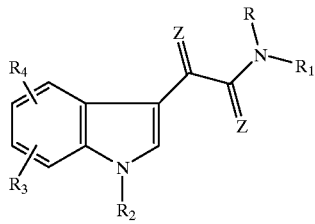

Formula I where the radicals R, $R_1$, $R_2$, $R_3$, $R_4$ and Z have the following meaning:

R=hydrogen, $(C_1–C_6)$-alkyl, where the alkyl group can be mono- or polysubstituted by the phenyl ring. This phenyl ring, for its part, can be mono- or polysubstituted by halogen, $(C_1–C_6)$-alkyl, $(C_3–C_7)$-cycloalkyl, by carboxyl groups, carboxyl groups esterified with $(C_1–C_6)$-alkanols, trifluoromethyl groups, hydroxyl groups, methoxy groups, ethoxy groups, benzyloxy groups and by a benzyl group which is mono- or polysubstituted in the phenyl moiety by $(C_1–C_6)$-alkyl groups halogen atoms or trifluoromethyl groups.

$R_1$ can be a phenyl ring which is mono- or polysubstituted by $(C_1–C_6)$-alkyl, $(C_1–C_6)$-alkoxy, hydroxyl, benzyloxy, nitro, amino, $(C_1–C_6)$-alkylamino, $(C_1–C_6)$-alkoxy-carbonylamino and by a carboxyl group or a carboxyl group esterified by $(C_1–C_6)$-alkanols, or is a pyridin structure of the formula II

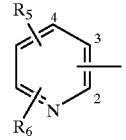

Formula II where the pyridin structure is alternatively bonded to the ring carbon atoms 2, 3 and 4 and can be substituted by the substitutents $R_5$ and $R_6$. The radicals $R_5$ and $R_6$ can be identical or different and have the meaning $(C_1–C_6)$-alkyl, and also the meaning $(C_3–C_7)$-cycloalkyl, $(C_1–C_6)$-alkoxy, nitro, amino, hydroxyl, halogen and trifluoromethyl and are furthermore the ethoxycarbonylamino radical and the group carboxyalkyloxy in which the alkyl group can have 1–4 C atoms.

$R_1$ can furthermore be a 2- or 4-pyrimidinyl-heterocycle or a pyridylmethyl radical in which $CH_2$ can be in the 2-, 3-, 4-position where the 2-pyrimidinyl ring can be mono- or polysubstituted by the methyl group, furthermore are [sic] the 2-, 3- and 4-quinolyl structure substituted by $(C_1–C_6)$-alkyl, halogen, the nitro group, the amino group and the $(C_1–C_6)$-alkylamino radical, or are [sic] a 2-, 3- and 4-quinolylmethyl group, where the ring carbons of the pyridylmethyl and quinolylmethyl radical can be substituted by $(C_1–C_6)$-alkyl, $(C_1–C_6)$-alkoxy, nitro, amino and $(C_1–C_6)$-alkoxycarbonylamino.

$R_1$ for the case where R is hydrogen or the benzyl group, can furthermore be the acid radical of a natural or unnatural amino acid, e.g. the α-glycyl, the α-sarcosyl, the α-alanyl, the α-leucyl, the α-isoleucyl, the α-seryl, the α-phenylalanyl, the α-histidyl, the α-prolyl, the α-arginyl, the α-lysyl, the α-asparagyl and the α-glutamyl radical, where the amino groups of the respective amino acids can be present in unprotected or protected form. Possible protective groups for the amino function are the carbobenzoxy radical (Z radical) and the tert-butoxycarbonyl radical (BOC radical) and also the acetyl group. In the case of the asparagyl and glutamyl radical claimed for $R_1$, the second, nonbonded carboxyl group is present as a free carboxyl group or in the form of an ester with $C_1–C_6$-alkanols, e.g. as the methyl, ethyl or as the tert-butyl ester. $R_1$ can furthermore be the allylaminocarbonyl-2-methylprop-1-yl group. R and $R_1$, together with the nitrogen atom to which they are bonded, can furthermore form a piperazine ring of the formula III or a homopiperazine ring if $R_1$ is an aminoalkylene group in which

Formula III $R_7$ is an alkyl radical, a phenyl ring which can be mono- or polysubstituted by $(C_1-C_6)$-alkyl, $(C_1-C_6)$-alkoxy, halogen, the nitro group, the amino function, by $(C_1-C_6)$-alkylamino, the benzhydryl group and the bis-p-fluorobenzylhydryl group.

$R_2$ can be hydrogen or the $(C_1-C_6)$-alkyl group, where the alkyl group can be mono- or polysubstituted by halogen and phenyl which for its part can be mono- or polysubstituted by halogen, $(C_1-C_6)$-alkyl, $(C_3-C_7)$-cycloalkyl, carboxyl groups, carboxyl groups esterified with $(C_1-C_6)$-alkanols, trifluoromethyl groups, hydroxyl groups, methoxy groups, ethoxy groups or benzyloxy groups. The $(C_1-C_6)$-alkyl group counting as $R_2$ can furthermore be substituted by the 2-quinolyl group and the 2-, 3- and 4-pyridyl structure, which in each case can both be mono- or polysubstituted by halogen, $(C_1-C_4)$-alkyl groups or $(C_1-C_4)$-alkoxy groups. $R_2$ is furthermore the aroyl radical, where the aroyl moiety on which this radical is based is the phenyl ring which can be mono- or polysubstituted by halogen $(C_1-C_6)$-alkyl, $(C_3-C_7)$-cycloalkyl, carboxyl groups, carboxyl groups esterified by $(C_1-C_6)$-alkanols, trifluoromethyl groups, hydroxyl groups, methoxy groups, ethoxy groups or benzyloxy groups.

$R_3$ and $R_4$ can be identical or different and are hydrogen, hydroxyl, $(C_1-C_6)$-alkyl, $(C_3-C_7)$-cycloalkyl, $(C_1-C_6)$-alkanoyl, $(C_1-C_6)$-alkoxy, halogen and benzyloxy. $R_3$ and $R_4$ can furthermore be the nitro group, the amino group, the $(C_1-C_4)$-mono- or dialkyl-substituted amino group, and the $(C_1-C_3)$-alkoxycarbonylamino function or $(C_1-C_3)$-alkcoxycarbonylamino-$(C_1-C_3)$-alkyl function.

Z is O or S

The designation alkyl, alkanol, alkoxy or alkylamino group for the radicals R, $R_1$, $R_2$, $R_3$, $R_4$, $R_5$, $R_6$ and $R_7$ is normally to be understood as meaning "straight-chain" and "branched" alkyl groups, where "straight-chain alkyl groups" can be, for example, radicals such as methyl, ethyl, n-propyl, n-butyl, n-pentyl and n-hexyl and "branched alkyl groups" designate, for example, radicals such as isopropyl or tert-butyl. "Cycloalkyl" is to be understood as meaning radicals such as, for example, cyclopropyl, cyclobutyl, cyclopentyl, cyclohexyl or cycloheptyl. The designation "halogen" represents fluorine, chlorine, bromine or iodine. The designation "alkoxy group" represents radicals such as, for example, methoxy, ethoxy, propoxy, butoxy, isopropoxy, isobutoxy or pentoxy.

The compounds according to the invention can also be present as acid addition salts, for example as salts of mineral acids, such as, for example, hydrochloric acid, sulfuric acid, phosphoric acid, salts of organic acids, such as, for example, acetic acid, lactic acid, malonic acid, maleic acid, fumaric acid, gluconic acid, glucuronic acid, citric acid, embonic acid, methanesulfonic acid, trifluoroacetic acid and succinic acid.

Both the compounds of the formula I and their salts are biologically active. The compounds of the formula 1 can be administered in free form or as salts with a physiologically tolerable acid. Administration can be carried out orally, parenterally, intravenously, transdermally or by inhalation.

The invention furthermore relates to pharmaceutical preparations containing at least one compound of the formula I or its salt with physiologically tolerable inorganic or organic acids and, if appropriate, pharmaceutically utilizable excipients and/or diluents or auxiliaries.

Suitable administration forms are, for example, tablets, coated tablets, capsules, solutions or ampoules, suppositories, patches, powder preparations which can be inhaled, suspensions, creams and ointments.

DETAILED DESCRIPTION OF THE INVENTION

The compounds according to the invention have a good antiasthmatic, antiallergic and immunosuppressant/immunomodulating action, for example in transplantations and diseases such as psoriasis, rheumatoid disorders and chronic polyarthritis, in the following pharmacological models:

Inhibition of the "Late Phase" Eosinophilia in the BAL 24 Hours After Allergen Challenge in Guinea Pigs Male guinea pigs (200–250 g, Dunkin Hartley Shoe) were actively sensitized subcutaneously with ovalbumin (10 μg of ovalbumin+1 mg of $Al(OH)_3$) and boosted 2 weeks later. One week after boosting with ovalbumin, the animals were exposed to an inhalation challenge with ovalbumin (0.5% strength solution) for 20–30 seconds. 24 hours later, the animals were killed by means of an overdose of urethane, exsanguinated and a bronchoalveolar lavage (BAL) was carried out using 2×5 ml of 0.9% strength physiological saline solution.

The lavage fluid was collected and centrifuged at 400 g for 10 minutes, and the pellets were suspended in 1 ml of 0.9% strength physiological saline solution. The eosinophils were counted microscopically in a Neubauer chamber after staining by means of Becton Dickinson test kit No. 5877. This test kit contains Phloxin B as a selective stain for eosinophils. The eosinophils in the BAL was [sic] counted here for each animal and expressed as eosinophils (millions/animal). For each group the mean value and standard deviation were determined. The percentage inhibition of eosinophilia for the group treated with test substance was calculated according to the following formula:

$(A-B)-(B-C)/(A-C)\times 100 = \%$ inhibition in this formula A eosinophils correspond to the untreated challenge group, B eosinophils to the treated group and C eosinophils to the unchallenged control group.

The animals were treated with a histamine $H_1$ antagonist (azelastine; 0.01 mg/kg p.o.) 2 hours before allergen challenge to avoid death. The administration of the test substances or of the vehicle was carried out 4 hours after allergen challenge. The percentage inhibition of eosinophilia in the BAL was calculated on groups of 6–10 animals.

TABLE

Inhibition of the "late phase" - eosinophilia 24 h after allergen challenge in guinea pigs

| Substance | Dose [mg/kg] | Administration | n | % Inhibition |
| --- | --- | --- | --- | --- |
| Cyclosporin A | 5 | i.p. + 4 h | 17 | 50.0 |
| | 10 | i.p. + 4 h | 11 | 47.0 |
| | 30 | p.o. + 4 h | 10 | 68.8 |
| According to Ex. 1 | 5 | i.p. + 4 h | 10 | 27.8 |
| | 10 | i.p. + 4 h | 10 | 55.4 |
| | 30 | p.o. + 4 h | 9 | 56.1 |

Assays for the Determination of Peptidylprolyl Isomerase (PPIase) Activity and Inhibition The PPIase activity of the cyclophilins was measured enzymatically according to Fischer et al. (1984). After isomerization of the substrate by the peptidyl prolyl isomerase, this is accessible to chymotrypsin, which cleaves the chromophore p-nitroaniline. For the determination of inhibition of the PPIase activity by substance, recombinant human Cyp B was used. The interaction of Cyp B with a potential inhibitor was carried out as follows:

A certain concentration of purified Cyp B was incubated with 1 μM substance for 15 min. The PPIase reaction was started by addition of the substrate solution to the reaction mixture which contains HEPES buffer, chymotrypsin and either test or control samples. Under these conditions, first-order kinetics were obtained with a constant $K_{observed}=K_0+K_{enz}$, where $K_0$ is the spontaneous isomerization and $K_{enz}$ is the rate of isomerization of the PPIase activity. The extinction values which correspond to the amount of the chromophore cleaved were measured using a Beckman DU 70 spectrophotometer at a constant reaction temperature of 10° C. The observed residual activity in the presence of various substances was compared with the cyclophilins only treated with solvent. The results were given in % residual activity. Cyclosporin A (CsA) was used as the reference compound. The inhibition of the PPIase activity was additionally checked by SDS-PAGE.

Colorimetric Assay (Based on the MTT Test) for the Non-Radioactive Quantification of Cell Proliferation and Survival Ability MTT is used for the quantitative determination of cell proliferation and activation, for example, in the reaction on growth factors and cytokines such as IL-2 and IL-4 and also for the quantification of the antiproliferative or toxic effects.

The assay is based on the cleavage of yellow tetrazolium salt MTT to give purple-red formazan crystals by metabolically active cells.

The cells, cultured in a 96-hole tissue culture plate, are incubated for about 4 h with yellow MTT solution. After this incubation time, purple-red formazan salt crystals are formed. These salt crystals are insoluble in aqueous solutions, but can be dissolved by addition of solubilizer and by incubation of the plates overnight.

The dissolved formazan product is quantified spectrophotometrically using an ELISA reader. An increase in the number of living cells results in an increase in the total metabolic activity in the sample. This increase correlates directly with the amount of the purple-red formazan crystals formed, which are [sic] measured by the absorption.

| Substance | Inhibition of PPIase activity [%] | Inhibition of CD3-induced IL-2 production [%] | | | Inhibition of lympho-proliferation [%] | | |
|---|---|---|---|---|---|---|---|
| Conc. [μM] | | 0.1 | 1 | 10 | 0.1 | 1 | 10 |
| According to Ex. 1 | 80–100 | 34 | 72 | 95 | 18 | 39 | 61 |
| Cyclosporin A | 80–100 | 56 | 82 | 94 | 8 | 7 | 11 |

The processes for the preparation of the compounds according to the invention are described in the following reaction schemes 1 and 2 and in general procedures. All compounds can be prepared as described or analogously.

The compounds of the general formula I are obtainable according to the following Scheme 1, shown for the synthesis of the compound Example 1:

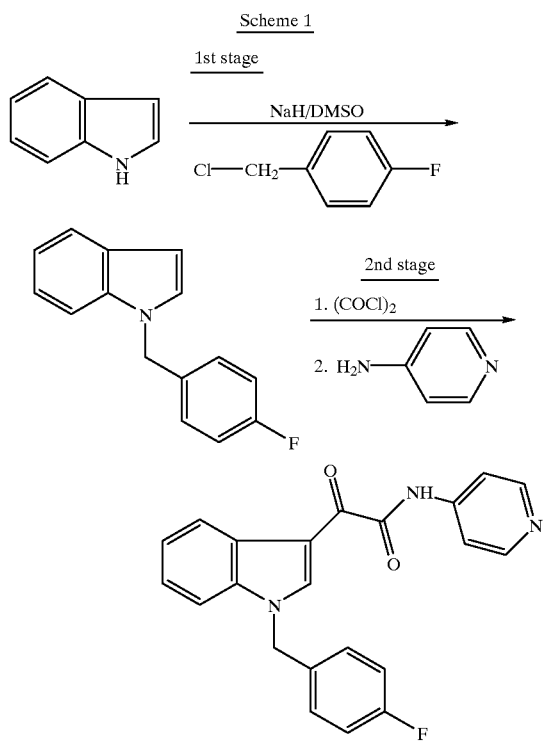

General Procedure for the Preparation of the Compounds of the General Formula I According to Scheme 1

1st Stage

The indole derivative, which can be unsubstituted or mono- or polysubstituted on C-2 or in the phenyl structure, is dissolved in a protic, dipolar aprotic or nonpolar organic solvent, such as, for example, isopropanol, tetrahydrofuran, dimethyl sulfoxide, dimethylformamide, dimethylacetamide, N-methylpyrrolidone, dioxane, toluene or methylene chloride and added dropwise to a suspension of a base in a molar or excess amount prepared in a 3-necked flask under an $N_2$ atmosphere, such as, for example, sodium hydride, powdered potassium hydroxide, potassium tert-butoxide, dimethylaminopyridine or sodium amide in a suitable solvent. The desired alkyl, aralkyl or heteroaralkyl halide, if appropriate with addition of a catalyst, such as, for example, copper, is then added and the mixture is reacted for some time, for example 30 minutes to 1.2 hours, and the temperature is kept within a range from 0° C. to 120° C., preferably between 30° C. to [sic] 80° C., particularly between 50° C. and 65° C. After completion of the reaction, the reaction mixture is added to water, the solution is extracted, for example, with diethyl ether, dichloromethane, chloroform, methyl tert-butyl ether or tetrahydrofuran and the organic phase obtained in each case is dried using anhydrous sodium sulfate. The organic phase is concentrated in vacuo, the residue which remains is crystallized by trituration or the oily residue is purified by recrystallization, distillation or by column or flash chromatography on silica gel or alumina. The eluent used is, for example, a mixture of dichloromethane and diethyl ether in the ratio 8:2 (vol/vol) or a mixture of dichloromethane and ethanol in the ratio 9:1 (vol/vol).

2nd Stage

The N-substituted indole obtained by the abovementioned 1st stage procedure is dissolved under a nitrogen atmosphere in an aprotic or nonpolar organic solvent, such as, for example, diethyl ether, methyl tert-butyl ether, tetrahydrofuran, dioxane, toluene, xylene, methylene chloride or chloroform and added to a solution, prepared under a nitrogen atmosphere, of a simply molar up to 60 percent excess amount of oxalyl chloride in an aprotic or nonpolar solvent, such as, for example, in diethyl ether, methyl tert-butylether, tetrahydrofuran, dioxane, toluene, xylene, methylene chloride or chloroform, the temperature being kept between −5° C. and 20° C. The reaction solution is then heated at a temperature between 10° C. and 130° C., preferably between 20° C. and 80° C., particularly between 30° C. and 50° C., for a period of 30 minutes up to 5 hours and the solvent is then evaporated. The residue of the "indolyl-3-glyoxylic acid chloride" formed in this manner which remains is dissolved in an aprotic solvent such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between 10° C. and −15° C., preferably between −5° C. and 0° C., and treated in the presence of an acid scavenger with a solution of the primary or secondary amine in a diluent.

Possible diluents are the solvents used above for the dissolution of the indolyl-3-glyoxylic acid chloride. Acid scavengers used are triethylamine, pyridin, dimethylaminopyridine, basic ion exchanger, sodium carbonate, potassium carbonate, powdered potassium hydroxide and excess primary or secondary amine employed for the reaction. The reaction takes place at a temperature from 0° C. to 120° C., preferably at 20–80° C., particularly between 40° C. and 60° C. After a reaction time of 1–3 hours and standing at room temperature for 24 hours, the hydrochloride of the acid scavenger is filtered, the filtrate is concentrated in vacuo, and the residue is recrystallized from an organic solvent or purified by column chromatography on silica gel or alumina. The eluent used is, for example, a mixture of dichloromethane and ethanol (95:5, vol/vol).

WORKING EXAMPLES

According to this general procedure for Stages 1 and 2, on which the synthesis Scheme 1 is based, the following compounds were synthesized which are evident from the following survey detailing the respective chemical name. In Table 1 which follows, the structures of these compounds and their melting points can be seen from the general formula I and the substituents $R_1$–$R_4$ and Z:

Example 1

N-(Pyridin-4-yl)-[1-(4-fluorobenzyl)indol-3-yl]glyoxylamide

1st Stage 1-(4-Fluorobenzyl)indole

A solution of 11.72 g (0.1 mol) of indole in 50 ml of dimethyl sulfoxide is added to a mixture of 2.64 g of sodium hydride (0.11 mol, mineral oil suspension) in 100 ml of dimethyl sulfoxide. The mixture is heated for 1.5 hours at 60° C., then allowed to cool and 15.9 g (0.11 mol) of 4-fluorobenzyl chloride are added dropwise. The solution is warmed to 60° C., allowed to stand overnight and then poured into 400 ml of water with stirring. The mixture is extracted several times with a total of 150 ml of methylene chloride, the organic phase is dried using anhydrous sodium sulfate and filtered, and the filtrate is concentrated in vacuo. The residue is distilled in a high vacuum: 21.0 g (96% of theory) B.p. (0.5 mm): 140° C.

2nd Stage

N-(pyridin-4-yl)-[1-(4-fluorobenzyl)indol-3-yl]glyoxylamide

A solution of 4.75 g (21.1 mmol) of 1-(4-fluorobenzyl)indole in 25 ml of ether is added dropwise at 0° C. and under $N_2$ to a solution of 2.25 ml of oxalyl chloride in 25 ml of ether. The mixture is refluxed for 2 hours and the solvent is then evaporated. 50 ml of tetrahydrofuran were [sic] then added to the residue, and the solution is cooled to −5° C. and treated dropwise with a solution of 4.66 g (49.5 mmol) of 4-aminopyridine in 200 ml of THF. The mixture is refluxed for 3 hours and allowed to stand at room temperature overnight. The 4-aminopyridine hydrochloride is filtered off with suction, the precipitate is washed with THF, the filtrate is concentrated in vacuo and the residue is recrystallized from ethyl acetate.

Yield: 7.09 g (90% of theory)

Melting point: 225–226° C.

Elemental analysis: Calc. C 70.77 H 4.32 N 11.25 Found C 71.09 H 4.36 N 11.26

Example 2

N-(Pyridin-4-yl)-(1-methylindol-3-yl)glyoxylamide

Example 3

N-(Pyridin-3-yl)-[1-(4-fluorobenzyl)indol-3-yl]glyoxylamide

Example 4

N-(Pyridin-3-yl)-(1-benzylindol-3-yl)glyoxylamide

Example 5

N-(Pyridin-3-yl)-[1-(2-chlorobenzyl)indol-3-yl]glyoxylamide

Example 6

N-(4-Fluorophenyl)-[1-(4-fluorobenzyl)indol-3-yl]glyoxylamide

Example 7

N-(4-Nitrophenyl)-[1-(4-fluorobenzyl)indol-3-yl]glyoxylamide

Example 8

N-(2-Chloropyridin-3-yl)-[1-(4-fluorobenzyl)indol-3-yl]glyoxylamide

Example 9

N-(Pyridin-4-yl)-(1-benzylindol-3-yl)glyoxylamide

Example 10

N-(Pyridin-4-yl)-[1-(3-pyridylmethyl)indol-3-yl]glyoxylamide

Example 11

N-(4-Fluorophenyl)-[1-(2-pyridylmethyl)indol-3-yl]glyoxylamide

Example 12

N-4(Fluorophenyl)-[1-(3-pyridylmethyl)indol-3-yl]glyoxylamide

Example 13

N-(Pyridin-4-yl)-[1-(4-chlorobenzyl)indol-3-yl]glyoxylamide

Example 14

N-(Pyridin-4-yl)-[1-(2-chlorobenzyl)indol-3-yl]glyoxylamide

Example 15

N-(Pyridin-2-yl)-[1-4-fluorobenzyl)indol-3-yl]glyoxylamide

Example 16

N-(Pyridin-4-yl)-[1-(2-pyridylmethyl)indol-3-yl]glyoxylamide

Example 17

(4-Phenylpiperazin-1-yl)-[1-(4-fluorobenzyl)indol-3-yl]glyoxylamide

Example 18

N-(Pyridin-2-yl)-(1-benzylindol-3-yl)glyoxylamide

Example 19

N-(Pyridin-4-yl)-[1-(4-fluorobenzyl)-6-ethoxycarbonylaminoindol-3-yl]glyoxylamide

Example 20

N-(Pyridin-4-yl)-[1-(4-fluorobenzyl)-5-ethoxycarbonylaminoindol-3-yl]glyoxylamide

Example 21

N-(Pyridin-4-yl)-[1-(4-fluorobenzyl)-6-cyclopentyloxycarbonylaminoindol-3-yl]glyoxylamide

Example 22

4-(Pyridin-4-yl)-piperazin-1-yl)-[1-(4-fluorobenzyl)indol-3-yl]-glyoxylamide

Example 23

N-(3,4,5-Trimethoxybenzyl)-N-(allylaminocarbonyl-2-methylprop-1-yl)-[1-(4-fluorobenzyl)indol-3-yl]glyoxylamide

Example 24

N-(Pyridin-4-yl)-[1-(4-fluorobenzyl)-5-methoxyindol-3-yl]glyoxylamide

Example 25

N-(Pyridin-4-yl)-[1-(4-fluorobenzyl)-5-hydroxyindol-3-yl]glyoxylamide

Example 26

N-pyridin-4-yl-[1-(4-fluorobenzyl)-5-ethoxycarbonylaminomethylindol-3-yl]glyoxylamide

TABLE 1

Novel indolylglyoxylamides according to reaction Scheme 1

Formula 1

| Example | R | $R_1$ | $R_2$ | $R_3$ | $R_4$ | Z | M.p. |
|---|---|---|---|---|---|---|---|
| Ex. 1 | H | 4-pyridyl-CH₂ | 4-F-C₆H₄-CH₂ | H | H | O | 225–6° C. |
| Ex. 2 | H | 4-pyridyl-CH₂ | CH₃ | H | H | O | 176° C. |
| Ex. 3 | H | 3-pyridyl-CH₂ | 4-F-C₆H₄-CH₂ | H | H | O | 173° C. |
| Ex. 4 | H | 4-pyridyl-CH₂ | C₆H₅-CH₂ | H | H | O | 140° C. |
| Ex. 5 | H | 3-pyridyl-CH₂ | 2-Cl-C₆H₄-CH₂ | H | H | O | 185° C. |
| Ex. 6 | H | 4-F-C₆H₄-CH₂ | 4-F-C₆H₄-CH₂ | H | H | O | 199° C. |

TABLE 1-continued

Novel indolylglyoxylamides according to reaction Scheme 1

Formula 1

| Example | R | R₁ | R₂ | R₃ | R₄ | Z | M.p. |
|---|---|---|---|---|---|---|---|
| Ex. 7 | H | 4-NO₂-C₆H₄-CH₃ | 4-F-C₆H₄-CH₂- | H | H | O | >250° C. |
| Ex. 8 | H | 2-Cl-3-CH₃-pyridyl | 4-F-C₆H₄-CH₂- | H | H | O | 149° C. |
| Ex. 9 | H | 4-CH₃-pyridyl | C₆H₅-CH₂- | H | H | O | 178–180° C. |
| Ex. 10 | H | 4-pyridyl | 3-pyridyl-CH₂- | H | H | O | 179° C. |
| Ex. 11 | H | 4-F-C₆H₄-CH₃ | 2-pyridyl-CH₂- | H | H | O | 132° C. |
| Ex. 12 | H | 4-F-C₆H₄-CH₃ | 3-pyridyl- | H | H | O | 144° C. |

TABLE 1-continued

Novel indolylglyoxylamides according to reaction Scheme 1

Formula 1

| Example | R | $R_1$ | $R_2$ | $R_3$ | $R_4$ | Z | M.p. |
|---|---|---|---|---|---|---|---|
| Ex. 13 | H | 4-pyridyl | -CH$_2$-(4-chlorophenyl) | H | H | O | 234° C. |
| Ex. 14 | H | 4-pyridyl | -CH$_2$-(2-chlorophenyl) | H | H | O | 184° C. |
| Ex. 15 | H | 2-pyridyl | -CH$_2$-(4-fluorophenyl) | H | H | O | 141° C. |
| Ex. 16 | H | 4-pyridyl | -CH$_2$-(2-pyridyl) | H | H | O | 202° C. |
| Ex. 17 | R + R$_1$ together: 4-piperidinyl-pyridyl | | -CH$_2$-(4-fluorophenyl) | H | H | O | 115° C. |
| Ex. 18 | H | 2-pyridyl | -CH$_3$ | H | H | O | 112–3° C. |

TABLE 1-continued

Novel indolylglyoxylamides according to reaction Scheme 1

Formula 1

| Example | R | R₁ | R₂ | R₃ | R₄ | Z | M.p. |
|---|---|---|---|---|---|---|---|
| Ex. 19 | H | 4-pyridyl | 4-F-C₆H₄-CH₂ | 6-NHCOOEt | H | O | >250° C. |
| Ex. 20 | H | 4-pyridyl | 4-F-C₆H₄-CH₂ | 5-NHCOOEt | H | O | 183° C. |
| Ex. 21 | H | 4-pyridyl | 4-F-C₆H₄-CH₂ | 6-NHCOO-cyclopentyl | H | O | oily |
| Ex. 22 | R + R₁ together = piperidinyl-pyridyl | | 4-F-C₆H₄-CH₂ | H | H | O | 160–62° C. |
| Ex. 23 | 3,4,5-trimethoxy-benzyl group shown | CH₃-CH(CH₃)-CH-C(O)NH-CH₂-CH=CH₂ | 4-F-C₆H₄-CH₂ | H | H | O | 139–141° C. |

TABLE 1-continued
Novel indolylglyoxylamides according to reaction Scheme 1
Formula 1
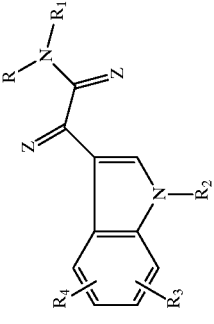
| Example | R | $R_1$ | $R_2$ | $R_3$ | $R_4$ | Z | M.p. |
|---|---|---|---|---|---|---|---|
| Ex. 24 | H | 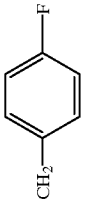 | 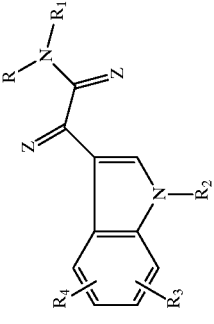  CH$_2$— | 5-OCH$_3$ | H | O | 188° C. |
| Ex. 25 | H | 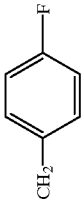 | 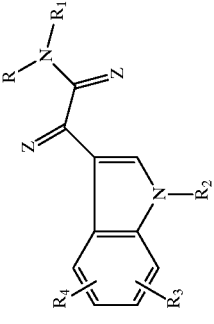  CH$_2$— | 5-OH | H | O | >250° C. |
| Ex. 26 | H | 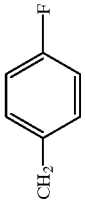 | 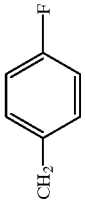  CH$_2$— | 6-CH$_2$—NHCOOEt | H | O | 175–176° C. |

Starting Materials for the Compounds of the General Formula 1 Prepared According to Synthesis Scheme 1, which come from Table 1

All precursors for the final synthesis stages of Examples 1 to 22 and 24 to 26 are commercially available.

Furthermore, the compounds of the general formula I are also obtainable according to the synthesis route of Scheme 2, shown by the synthesis of the compound Example 27:

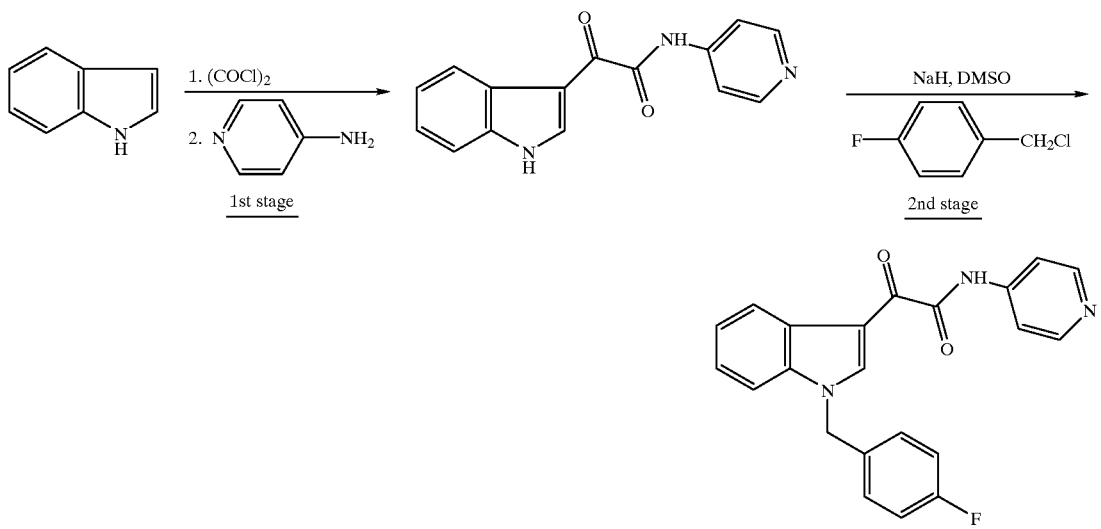

Scheme 2

General Procedure for the Preparation of the Compounds of the General Formula 1 According to Scheme 2
1st Stage The indole derivative dissolved in a solvent, such as given above for oxalyl chloride, which can be unsubstituted or substituted on C-2 or in the phenyl ring, is added dropwise at a temperature between −5° C. and +5° C. to a solution of a simply molar up to 60% excess amount of oxalyl chloride prepared under a nitrogen atmosphere in an aprotic or nonpolar solvent, such as, for example, in diethyl ether, methyl tert-butyl ether, tetrahydrofuran, dioxane or alternatively dichloromethane. The reaction solution is then heated for 1 to 5 hours to a temperature between 10° C. and 120° C., preferably between 20° C. and 80° C., particularly between 30° C. and 60° C., and the solvent is then evaporated. The residue of the (indol-3-yl)glyoxylic acid chloride which remains is dissolved or suspended in an aprotic solvent, such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between −10° C. and +10° C., preferably to −5° C. to 0° C., and treated with a solution of the primary or secondary amine in a diluent in the presence of an acid scavenger. Possible diluents are the solvents used for the dissolution of the "indolyl-3-glyoxylic acid chloride". Acid scavengers used are triethylamine, pyridin, dimethylaminopyridine, basic ion exchanger, sodium carbonate, potassium carbonate, powdered potassium hydroxide and excess primary or secondary amine employed for the reaction. The reaction takes place at a temperature from 0° C. to 120° C., preferably at 20–80° C., particularly between 40° C. and 60° C. After a reaction time of 1–4 hours and standing at room temperature for 24 hours, the precipitate is digested with water, and the solid is filtered off with suction and dried in vacuo. The desired compound is purified by recrystallization in an organic solvent or by column chromatography on silica gel or alumina. The solvent used is, for example, a mixture of dichloromethane and ethanol (10:1, vol/vol).

2nd Stage

The "indol-3-ylglyoxylamide" obtained according to the abovementioned 1st Stage procedure is dissolved in a protic, dipolar aprotic or nonpolar organic solvent, such as, for example, in isopropanol, tetrahydrofuran, dimethyl sulfoxide, dimethylformamide, dimethylacetamide, N-methylpyrrolidone, dioxane, toluene or methylene chloride and added dropwise to a suspension of a base such as, for example, sodium hydride, powdered potassium hydroxide, potassium tert-butoxide, dimethylaminopyridine or sodium amide in a suitable solvent, in a molar amount or in excess prepared in a 3-necked flask under an $N_2$ atmosphere. The desired alkyl, aralkyl or heteroaralkyl halide is then added either in undiluted form or in a diluent which was also used, for example, to dissolve the "indol-3-yl glyoxylamide", if appropriate with addition of a catalyst, such as, for example, copper, and the mixture is allowed to react for some time, e.g. 30 minutes to 12 hours, and the temperature is kept within a range between 0° C. and 120° C., preferably between 30° C. and 80° C., particularly between 50 and 70° C. After completion of the reaction, the reaction mixture is added to water, the solution is extracted, for example, with diethyl ether, dichloromethane, chloroform, methyl tert-butyl ether, tetrahydrofuran or N-butanol and the organic phase obtained in each case is dried using anhydrous sodium sulfate. The organic phase is concentrated in vacuo, the residue which remains is crystallized by trituration or the oily residue is purified by distillation or by column chromatography or flash chromatography on silica gel or alumina. The eluent used is, for example, a mixture of methylene chloride and diethyl ether in the ratio 8:2 (vol/vol) or a mixture of methylene chloride and ethanol in the ratio 9:1 (v/v).

WORKING EXAMPLES

According to this general procedure for Stages 1 and 2, on which synthesis Scheme 2 is based, compounds were synthesized which have already been prepared according to the synthesis course of reaction Scheme 1 and are evident from Table 1. The relevant precursors of these compounds are evident from Table 2.

Example 27

N-(pyridin-4-yl)-[1-(4-flurobenzyl)indol-3-yl] glyoxylamide (Final substance, identical to Example 1)
1st Stage N-(Pyridin-4-yl)-(indol-3-yl)glyoxylamide A solution of 10 g (85.3 mmol) of indole in 100 ml of ether is added dropwise at 0° C. to a solution of 9 ml of oxalyl chloride in 100 ml of anhydrous ether. The mixture is kept under reflux for 3 hours. A suspension of 12 g (127.9 mmol) of 4-aminopyridine in 500 ml of tetrahydrofuran is then added dropwise at −5° C., and the reaction mixture is heated to reflux temperature with stirring for 3 hours and allowed to stand overnight at room temperature. The precipitate is filtered and treated with water and the dried compound is purified on a silica gel column (silica gel 60, Merck AG, Darmstadt) using the eluent methylene chloride/ethanol (10:1, v/v).

Yield: 9.8 g (43.3% of theory)
M.p.: from 250° C.
2nd Stage

N-(Pyridin-4-yl)-[1-[4-fluorobenzylindol-3-yl] glyoxylamide

The N-(pyridin-4-yl)-(indol-3-yl)glyoxylamide obtained according to the 1st stage is reacted with 4-fluorobenzyl chloride according to the "benzylation procedure" (Page 11) and the compound obtained is isolated.

Yield: 41% of theory
M.p.: 224–225° C.
Elemental analysis: Calc. C 70.77 H 4.32 N 11.25 Found C 70.98 H 4.40 N 11.49

Example 28

N-(4-Nitrophenyl)-[1-(4-fluorobenzyl)indol-3-yl] glyoxylamide (Final substance, identical to Example 7)

Example 29

N-(4-Fluorophenyl)-[1-(4-fluorobenzyl)indol-3-yl] glyoxylamide (Final substance, identical to Example 6)

Example 30

N-)Pyridin-3-yl)-[1-(4-fluorobenzyl)indol-3-yl] glyoxylamide (Final substance, identical to Example 3)

The following precursors (1st stage of reaction scheme 2, Table 2) were obtained according to the present Scheme 2.

Example 31

N-(Pyridin-4-yl)-(indol-3-yl)glyoxylamide

Example 32

N-(4-Nitrophenyl)-(indol-3-yl)glyoxylamide

Example 33

N-(4-Fluorophenyl)-(indol-3-yl)glyoxylamide

Example 34

N-(Pyridin-3-yl)-(indol-3-yl)glyoxylamide

TABLE 2

Novel indolylglyoxylamides according to reaction Scheme 2

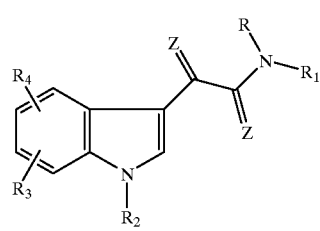

Formula 1

| Example | R | $R_1$ | $R_2$ | $R_3$ | $R_4$ | Z | M.p. |
|---|---|---|---|---|---|---|---|
| Ex. 31 | H | 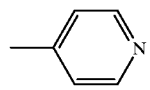 | H | H | H | O | >250° C. |

TABLE 2-continued

Novel indolylglyoxylamides according to reaction Scheme 2

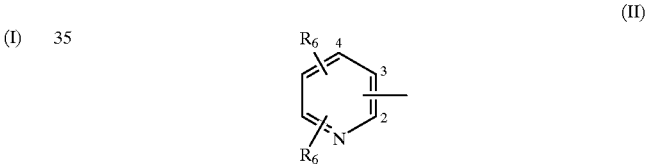

Formula 1

| Example | R | R₁ | R₂ | R₃ | R₄ | Z | M.p. |
|---|---|---|---|---|---|---|---|
| Ex. 32 | H | 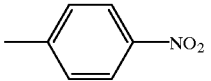 | H | H | H | O | >250° C. |
| Ex. 33 | H | 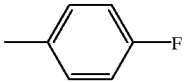 | H | H | H | O | 233–5° C. |
| Ex. 34 | H | 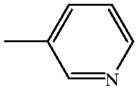 | H | H | H | O | 235° C. |

What is claimed is:

1. An N-substituted indol-3-glyoxylamide of formula I:

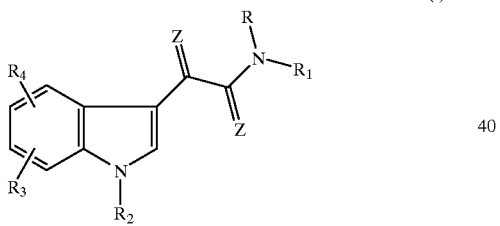

(I)

or an acid addition salt thereof, wherein the radicals R, $R_1$, $R_2$, $R_3$, $R_4$ and Z have the following meanings:

R represents
(1) hydrogen, or
(2) $(C_1-C_4)$-alkyl, wherein the alkyl group is optionally mono- or polysubstituted by a phenyl ring,
which ring is optionally mono- or polysubstituted by halogen, $(C_1-C_6)$-alkyl, $(C_3-C_7)$-cycloalkyl, carbonyl groups, carboxyl groups esterified with $(C_1-C_6)$-alkanols, trifluoromethyl groups, hydroxyl groups, methoxy groups, ethoxy groups, benzyloxy groups and benzyl groups which are optionally mono- or polysubstituted on the phenyl moiety by $(C_1-C_6)$alkyl groups, halogen atoms or trifluoromethyl groups;

$R_1$ represents
(1) a phenyl ring which is mono- or polysubstituted by $(C_1-C_6)$-alkyl, $(C_1-C_6)$-alkoxy, hydroxyl, benzyloxy, nitro, amino, $(C_1-C_6)$-alkylamino, $(C_1-C_6)$-alkoxy-carbonylamino and by a carboxyl group or a carboxyl group esterified by a $(C_1-C_6)$-alkanol;

(2) a pyridine structure of formula II:

(II)

wherein the pyridine structure is alternatively bonded to the ring carbon atoms 2, 3 and 4 and is optionally substituted by $R_5$ and $R_6$, which may be identical or different and represent $(C_1-C_6)$-alkyl, $(C_3-C_7)$ cycloalkyl, $(C_1-C_6)$alkoxy, nitro, amino, hydroxyl, halogen, trifluromethyl, an ethoxycarbonylamino radical and a carboxyalkyloxy group in which the alkyl group has 1–4 carbon atoms;

(3) a pyridylmethyl radical in which $CH_2$ is in the 2-, 3- or 4-position;

(4) a 2-, 3- or 4-quinolyl structure substituted by $(C_1-C_6)$-alkyl, halogen, a nitro group, an amino group or a $(C_1-C_6)$-alkylamino radical;

(5) a 2-, 3- or 4-quinolyl methyl group, wherein the ring carbons of the pyridylmethyl and quinolylmethyl radicals are optionally substituted by $(C_1-C_6)$-alkyl, $(C_1-C_6)$-alkoxy, nitro, amino and $(C_1-C_6)$-alkoxycarbonylamino;

(6) if R represents hydrogen or a benzyl group, $R_1$ can represent the acid radical of a natural amino acid, wherein the amino group of said amino acid is present in protected or unprotected form wherein if $R_1$ represents an asparagyl or a glutamyl radical having a second nonbonded carboxyl group, said nonbonded carboxyl group is present as a free carboxyl group or in the form of an ester with $C_1-C_6$-alkanols;

(7) an allylaminocarbonyl-2-methylprop-1-yl group;
R$_2$ represents
(1) hydrogen;
(2) a (C$_1$–C$_6$)-alkyl group,
said alkyl group being optionally mono- or polysubstituted by halogen or a phenyl ring,
which ring is optionally mono- or polysubstituted by halogen, (C$_1$–C$_6$)-alkyl, (C$_3$–C$_7$)-cycloalkyl, carbonyl groups, carboxyl groups esterified with (C$_1$–C$_6$)-alkanols, trifluoromethyl groups, hydroxyl groups, methoxy groups, ethoxy groups, or benzyloxy groups;
or by a 2-quinolyl group or a 2-, 3- or 4-pyridyl structure which are optionally mono- or polysubstituted by halogen, (C$_1$–C$_4$)-alkyl groups or (C$_1$–C$_4$)-alkoxy groups;
(3) an aroyl radical, wherein the aroyl moiety on which the radical is based is a phenyl ring which is optionally mono- or polysubstituted by halogen, (C$_1$–C$_6$)-alkyl, (C$_3$–C$_7$)-cycloalkyl, carbonyl groups, carboxyl groups esterified with (C$_1$–C$_6$)-alkanols, trifluoromethyl groups, hydroxyl groups, methoxy groups, ethoxy groups, or benzyloxy groups;
R$_3$ and R$_4$, which are identical or different, represent hydrogen, hydroxyl, (C$_1$–C$_6$)-alkyl, (C$_3$–C$_7$)-cycloalkyl, (C$_1$–C$_6$)-alkanoyl, (C$_1$–C$_6$)-alkoxy, halogen, benzoxy, a nitro group, an amino group, a (C$_1$–C$_4$)-mono- or dialkyl substituted amino group, a (C$_1$–C$_3$)-alkoxycarbonylamino function or a (C$_1$–C$_3$)-alkoxycarbonylamino-(C$_1$–C$_3$)-alkyl function; and
Z represents O or S;
wherein alkyl, alkanol, alkoxy and alkylamino groups may be straight chained or branched.

2. The N-substituted indol-3-glyoxylamide of claim 1 wherein R is hydrogen or a benzyl group and R$_1$ is the acid radical of an amino acid selected from the group consisting of α-glycyl, α-alanyl, α-leucyl, α-isoleucyl, α-seryl, α-phenylalanyl, α-arginyl, α-lysyl, α-asparagyl and α-glutamyl.

3. A compound according to claim 1 selected from the group consisting of:
N-(Pyridin-4-yl)-[1-(4-fluorobenzyl)indol-3-yl]glyoxylamide
N-(Pyridin-4-yl)-(4-methylindol-3-yl)glyoxylamide
N-(Pyridin-3-yl)-[1-(4-fluorobenzyl)-indol-3-yl]glyoxylamide
N-(Pyridin-3-yl)-(1-benzylindol-3-yl)glyoxylamide
N-(Pyridin-3-yl)-[1-(2-chorobenzyl)indol-3-yl]glyoxylamide
N-(4-Fluorophenyl)-[1-(4-fluorobenzyl)indol-3-yl]glyoxylamide
N-(4-Nitrophenyl)-[1-(4-fluorobenzyl)indol-3-yl]glyoxylamide
N-(2-Chloropyridine-3-yl)-[1-(4-fluorobenzyl)indol-3-yl]glyoxylamide
N-(Pyridin-4-yl)-(-benzylindol-3-yl)glyoxylamide
N-(Pyridin-4-yl)-[1-(3-pyridylmethyl)indol-3-yl]glyoxylamide
N-(4-Fluorophenyl)-[1-(2-pyridylmethyl)indol-3-yl]glyoxylamide
N-(4-Fluorophenyl)-[1-(3-pyridylmethyl)indol-3-yl]glyoxylamide
N-(Pyridin-4-yl)-[1-(4-chlorobenzyl)indol-3-yl]glyoxylamide
N-(Pyridin-4-yl)-[1-(2-chlorobenzyl)indol-3-yl]glyoxylamide
N-(Pyridin-2-yl)-[1-(4-fluorobenzyl)indol-3-yl]glyoxylamide
N-(Pyridin-4-yl)-[1-(2-pyridylmethyl)indol-3-yl]glyoxylamide
N-(Pyridin-2-yl)-(1-benzylindol-3-yl)glyoxylamide
N-(Pyridin-4-yl)-[1-(4-fluorobenzyl)-6-ethoxycarbonylaminoindol-3-yl]glyoxylamide
N-(Pyridin-4-yl)-[1-(4-fluorobenzyl)-5-ethoxycarbonylaminoindol-3-yl]glyoxylamide
N-(Pyridin-4-)-[1-(4-fluorobenzyl)-6-cyclopentyloxycarbonylaminoindol-3-yl]glyoxylamide
N-(3,4,5-Trimethoxybenzyl)-N-(allylaminocarbonyl-2-methylprop-1-yl)-[1-(4-fluorobenzyl)indol-3-yl]glyoxylamide
N-(Pyridin-4-yl)-[1-(4-fluorobenzyl)-5-methoxyindol-3-yl]glyoxylamide
N-(Pyridin-4-yl)-[1-(4-fluorobenzyl)-5-hydroxyindol-3-yl]glyoxylamide
N-(Pyridin-4-yl-[1-(4-fluorobenzyl)-5-ethoxycarbonylaminomethylindol-3-yl]glyoxylamide.

4. Medicaments comprising at least one compound of the formula I according to one of claims 1 or 3 in addition to customary excipients and/or diluents or auxiliaries.

5. Process for the production of a medicament, wherein a compound of the formula I according to one of claims 1 or 3 is processed with customary pharmaceutical excipients and/or diluents or other auxiliaries to give pharmaceutical preparations or brought into a therapeutically useable form.

6. Medicaments according to one of claims 1 or 3 in the form of tablets, coated tablets, capsules, solutions or ampoules, suppositories, patches, powder preparations which can be employed by inhalation, suspensions, creams and ointments.

7. Process for the preparation of N-substituted indole-3-glyoxylamides of the formula I according to claims 1 and 3, in which R, R$_1$, R$_2$, R$_3$, R$_4$ and Z have the meaning mentioned in claim 1, wherein a) an indole derivative of the formula IV

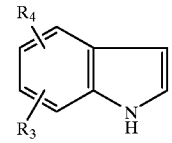

IV in which R$_3$ and R$_4$ have the meaning mentioned, is added to a suspended base in a protic, dipolar aprotic or nonpolar organic solvent, reacted with a reactive compound which carries the radical R$_2$ and where R$_2$ has the meaning mentioned, the 1-indole derivative of the formula V

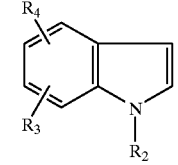

V in which R$_2$, R$_3$ and R$_4$ have the meaning mentioned, is reacted with a reactive compound of the formula VI (C—Z—Hal)$_2$    VI in which Z has the meaning oxygen and Hal is a halogen fluorine, chlorine, bromine or iodine, and then with a primary or secondary amine of the formula VII

HNRR₁                                          VII in which R and R₁ have the meaning mentioned, in an aprotic or dipolar aprotic solvent and the target compound of the formula I is isolated, or b) an indole derivative of the formula IV

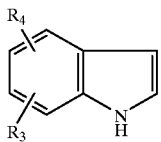
IV in which R₃ and R₄ have the meaning mentioned, is reacted in an aprotic or nonpolar solvent with a reactive compound of the formula VI (C—Z—Hal)₂                                     VI in which Z has the meaning oxygen and Hal is a halogen fluorine, chlorine, bromine or iodine, and then in an aprotic or dipolar aprotic solvent with a primary or secondary amine of the formula VII

HNRR₁                                          VII in which R and R₁ have the meaning mentioned, and then the 3-indole derivative of the formula VIII

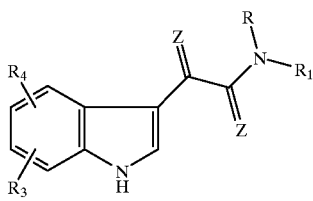
VIII in which R, R₁, R₂, R₃, R₄ and Z have the meaning mentioned, is reacted in a protic, dipolar aprotic or nonpolar organic solvent in the presence of a suspended base with a reactive compound which carries the radical R₂ and where R₂ has the meaning mentioned, and the target compound of the formula I is isolated.

8. The N-substituted indol-3-glyoxylamide of claim 2 wherein R represents hydrogen or a benzyl group and R₁ represents α-asparagyl or α-glutamyl, in which the non-bonded carboxyl group is a methyl, ethyl or tert-butyl ester.

9. The N-substituted indol-3-glyoxylamide of claim 2 wherein R represents hydrogen or a benzyl group and R₁ represents the acid radical of a natural amino acid protected by a carbobenzoxy radical, a tert-butoxycarbonyl radical or an acetyl group.

10. A method of treating asthma and/or allergy in a mammal comprising the step of administering to said mammal a treatment-effective amount of a compound of formula I:

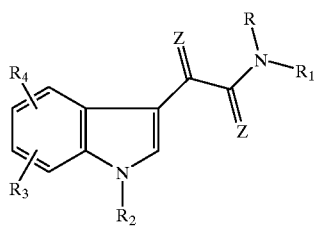
(I)

or an acid addition salt thereof, wherein the radicals R, R₁, R₂, R₃, R₄ and Z have the following meanings:

R represents
(1) hydrogen, or
(2) (C₁–C₄)-alkyl, wherein the alkyl group is optionally mono- or polysubstituted by a phenyl ring,
which ring is optionally mono- or polysubstituted by halogen, (C₁–C₆)-alkyl, (C₃–C₇)-cycloalkyl, carbonyl groups, carboxyl groups esterified with (C₁–C₆)-alkanols, trifluoromethyl groups, hydroxyl groups, methoxy groups, ethoxy groups, benzyloxy groups and benzyl groups which are optionally mono- or polysubstituted on the phenyl moiety by (C₁–C₆)alkyl groups, halogen atoms or trifluoromethyl groups;

R₁ represents
(1) a phenyl ring which is mono- or polysubstituted by (C₁–C₆)-alkyl, (C₁–C₆)-alkoxy, hydroxyl, benzyloxy, nitro, amino, (C₁–C₆)-alkylamino, (C₁–C₆)-alkoxy-carbonylamino and by a carboxyl group or a carboxyl group esterified by a (C₁–C₆)-alkanol;
(2) a pyridine structure of formula II:

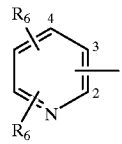
(II)

wherein the pyridine structure is alternatively bonded to the ring carbon atoms 2, 3 and 4 and is optionally substituted by R₅ and R₆, which may be identical or different and represent (C₁–C₆)-alkyl, (C₃–C₇) cycloalkyl, (C₁–C₆)alkoxy, nitro, amino, hydroxyl, halogen, trifluromethyl, an ethoxycarbonylamino radical and a carboxyalkyloxy group in which the alkyl group has 1–4 carbon atoms;
(3) a pyridylmethyl radical in which CH₂ is in the 2-, 3- or 4-position;
(4) a 2-, 3- or 4-quinolyl structure substituted by (C₁–C₆)-alkyl, halogen, a nitro group, an amino group or a (C₁–C₆)-alkylamino radical;
(5) a 2-, 3- or 4-quinolyl methyl group, wherein the ring carbons of the pyridylmethyl and quinolylmethyl radicals are optionally substituted by (C₁–C₆)-alkyl, (C₁–C₆)-alkoxy, nitro, amino and (C₁–C₆)-alkoxy-carbonylamino;
(6) if R represents hydrogen or a benzyl group, R₁ can represent the acid radical of a natural amino acid, wherein the amino group of said amino acid is present in protected or unprotected form wherein if R₁ represents an asparagyl or a glutamyl radical having a second nonbonded carboxyl group, said nonbonded carboxyl group is present as a free carboxyl group or in the form of an ester with $C_1$–$C_6$-alkanols;

(7) an allylaminocarbonyl-2-methylprop-1-yl group;

$R_2$ represents
(1) hydrogen;
(2) a ($C_1$–$C_6$)-alkyl group,
said alkyl group being optionally mono- or polysubstituted by halogen or a phenyl ring,
which ring is optionally mono- or polysubstituted by halogen, ($C_1$–$C_6$)-alkyl, ($C_3$–$C_7$)-cycloalkyl, carbonyl groups, carboxyl groups esterified with ($C_1$–$C_6$)-alkanols, trifluoromethyl groups, hydroxyl groups, methoxy groups, ethoxy groups, or benzyloxy groups;
or by a 2-quinolyl group or a 2-, 3- or 4-pyridyl structure which are optionally mono- or polysubstituted by halogen, ($C_1$–$C_4$)-alkyl groups or ($C_1$–$C_4$)-alkoxy groups;
(3) an aroyl radical, wherein the aroyl moiety on which the radical is based is a phenyl ring which is optionally mono- or polysubstituted by halogen, ($C_1$–$C_6$)-alkyl, ($C_3$–$C_7$)-cycloalkyl, carbonyl groups, carboxyl groups esterified with ($C_1$–$C_6$)-alkanols, trifluoromethyl groups, hydroxyl groups, methoxy groups, ethoxy groups, or benzyloxy groups;

$R_3$ and $R_4$, which are identical or different, represent hydrogen, hydroxyl, ($C_1$–$C_6$)-alkyl, ($C_3$–$C_7$)-cycloalkyl, ($C_1$–$C_6$)-alkanoyl, ($C_1$–$C_6$)-alkoxy, halogen, benzoxy, a nitro group, an amino group, a ($C_1$–$C_4$)-mono- or dialkyl substituted amino group, a ($C_1$–$C_3$)-alkoxycarbonylamino function or a ($C_1$–$C_3$)-alkoxycarbonylamino-($C_1$–$C_3$)-alkyl function; and Z represents O or S;
wherein alkyl, alkanol, alkoxy and alkylamino groups may be straight chained or branched.

11. A method of inducing regression of an immunological reaction in a mammal comprising the step of administering to said mammal an effective amount of a compound according to formula I:

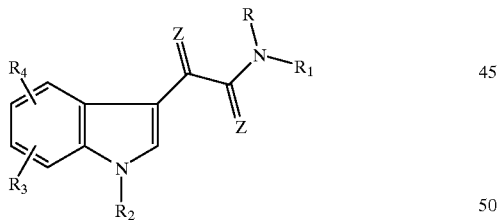

(I)

or an acid addition salt thereof, wherein the radicals R, $R_1$, $R_2$, $R_3$, $R_4$ and Z have the following meanings:

R represents
(1) hydrogen, or
(2) ($C_1$–$C_4$)-alkyl, wherein the alkyl group is optionally mono- or polysubstituted by a phenyl ring,
which ring is optionally mono- or polysubstituted by halogen, ($C_1$–$C_6$)-alkyl, ($C_3$–$C_7$)-cycloalkyl, carbonyl groups, carboxyl groups esterified with ($C_1$–$C_6$)-alkanols, trifluoromethyl groups, hydroxyl groups, methoxy groups, ethoxy groups, benzyloxy groups and benzyl groups which are optionally mono- or polysubstituted on the phenyl moiety by ($C_1$–$C_6$)alkyl groups, halogen atoms or trifluoromethyl groups;

$R_1$ represents
(1) a phenyl ring which is mono- or polysubstituted by ($C_1$–$C_6$)-alkyl, ($C_1$–$C_6$)-alkoxy, hydroxyl, benzyloxy, nitro, amino, ($C_1$–$C_6$)-alkylamino, ($C_1$–$C_6$)-alkoxy-carbonylamino and by a carboxyl group or a carboxyl group esterified by a ($C_1$–$C_6$)-alkanol;
(2) a pyridine structure of formula II:

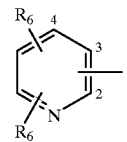

(II)

wherein the pyridine structure is alternatively bonded to the ring carbon atoms 2, 3 and 4 and is optionally substituted by $R_5$ and $R_6$, which may be identical or different and represent ($C_1$–$C_6$)-alkyl, ($C_3$–$C_7$) cycloalkyl, ($C_1$–$C_6$)alkoxy, nitro, amino, hydroxyl, halogen, trifluromethyl, an ethoxycarbonylamino radical and a carboxyalkyloxy group in which the alkyl group has 1–4 carbon atoms;
(3) a pyridylmethyl radical in which $CH_2$ is in the 2-, 3- or 4-position;
(4) a 2-, 3- or 4-quinolyl structure substituted by ($C_1$–$C_6$)-alkyl, halogen, a nitro group, an amino group or a ($C_1$–$C_6$)-alkylamino radical;
(5) a 2-, 3- or 4-quinolyl methyl group, wherein the ring carbons of the pyridylmethyl and quinolylmethyl radicals are optionally substituted by ($C_1$–$C_6$)-alkyl, ($C_1$–$C_6$)-alkoxy, nitro, amino and ($C_1$–$C_6$)-alkoxycarbonylamino;
(6) if R represents hydrogen or a benzyl group, $R_1$ can represent the acid radical of a natural amino acid, wherein the amino group of said amino acid is present in protected or unprotected form wherein if $R_1$ represents an asparagyl or a glutamyl radical having a second nonbonded carboxyl group, said nonbonded carboxyl group is present as a free carboxyl group or in the form of an ester with $C_1$–$C_6$-alkanols;
(7) an allylaminocarbonyl-2-methylprop-1-yl group;

$R_2$ represents
(1) hydrogen;
(2) a ($C_1$–$C_6$)-alkyl group,
said alkyl group being optionally mono- or polysubstituted by halogen or a phenyl ring,
which ring is optionally mono- or polysubstituted by halogen, ($C_1$–$C_6$)-alkyl, ($C_3$–$C_7$)-cycloalkyl, carbonyl groups, carboxyl groups esterified with ($C_1$–$C_6$)-alkanols, trifluoromethyl groups, hydroxyl groups, methoxy groups, ethoxy groups, or benzyloxy groups;
or by a 2-quinolyl group or a 2-, 3- or 4-pyridyl structure which are optionally mono- or polysubstituted by halogen, ($C_1$–$C_4$)-alkyl groups or ($C_1$–$C_4$)-alkoxy groups;
(3) an aroyl radical, wherein the aroyl moiety on which the radical is based is a phenyl ring which is optionally mono- or polysubstituted by halogen, ($C_1$–$C_6$)-alkyl, ($C_3$–$C_7$)-cycloalkyl, carbonyl groups, carboxyl groups esterified with ($C_1$–$C_6$)-alkanols, trifluoromethyl groups, hydroxyl groups, methoxy groups, ethoxy groups, or benzyloxy groups;

$R_3$ and $R_4$, which are identical or different, represent hydrogen, hydroxyl, $(C_1-C_6)$-alkyl, $(C_3-C_7)$-cycloalkyl, $(C_1-C_6)$-alkanoyl, $(C_1-C_6)$-alkoxy, halogen, benzoxy, a nitro group, an amino group, a $(C_1-C_4)$-mono- or dialkyl substituted amino group, a $(C_1-C_3)$-alkoxycarbonylamino function or a $(C_1-C_3)$-alkoxycarbonylamino-$(C_1-C_3)$-alkyl function; and Z represents O or S;

wherein alkyl, alkanol, alkoxy and alkylamino groups may be straight chained or branched.

* * * * *

UNITED STATES PATENT AND TRADEMARK OFFICE
CERTIFICATE OF CORRECTION

PATENT NO.  : 6,008,231
DATED       : December 28, 1999
INVENTOR(S) : Lebaut et al.

It is certified that error appears in the above-identified patent and that said Letters Patent is hereby corrected as shown below:

Column 5, claim 1,
Line 50, change "$(C_1-C_4)$-alkyl" to -- $(C_1-C_6)$-alkyl -- ;
Lines 53-54, change "carbonyl" to "carboxyl -- ;

Column 27,
Line 9, change "carbonyl" to "carboxyl -- ;

Column 30, claim 10
Line 17, change "$(C_1-C_4)$-alkyl" to -- $(C_1-C_6)$-alkyl -- ;

Column 31,
Line 13, change "carbonyl" to "carboxyl -- ;
Line 24, change "carbonyl" to "carboxyl -- ;

Claim 11,
Line 57 change "$(C_1-C_4)$-alkyl" to -- $(C_1-C_6)$-alkyl -- ;
Line 60-61, change "carbonyl" to "carboxyl -- ;

Column 32,
Line 53, change "carbonyl" to "carboxyl -- ;
Line 64, change "carbonyl" to "carboxyl -- .

Signed and Sealed this

Twenty-eighth Day of August, 2001

Attest:

*Nicholas P. Godici*

NICHOLAS P. GODICI
*Attesting Officer*          *Acting Director of the United States Patent and Trademark Office*

UNITED STATES PATENT AND TRADEMARK OFFICE
CERTIFICATE OF CORRECTION

PATENT NO. : 6,008,231 C1
APPLICATION NO. : 90/009054
DATED : March 3, 2009
INVENTOR(S) : Le Baut et al.

It is certified that error appears in the above-identified patent and that said Letters Patent is hereby corrected as shown below:

In claim 1, column 1, lines 30-39, please replace

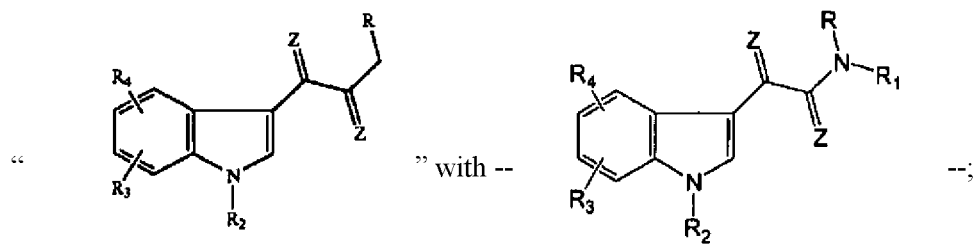

In claim 1, column 1, line 48, please replace "$(C_1-C_6)$-alkyl," with --$(C_1-C_4)$-alkyl,--;

In claim 1, column 1, line 52, please replace "carboxyl" with --carbonyl--;

In claim 1, column 2, line 15, please replace "carboxyl alkyloxy" with --carboxyalkyloxy--;

In claim 1, column 2, line 38, please replace "[(2]*l*)" with --([2]*l*)--.

Signed and Sealed this

Ninth Day of February, 2010

David J. Kappos
*Director of the United States Patent and Trademark Office*

(12) EX PARTE REEXAMINATION CERTIFICATE (6685th)
United States Patent
Lebaut et al.

(10) Number: US 6,008,231 C1
(45) Certificate Issued: *Mar. 3, 2009

(54) N-SUBSTITUTED INDOLE-3 GLYOXYLAMIDES HAVING ANTI-ASTHMATIC ANTIALLERGIC AND IMMUNOSUPPRESSANT/ IMMUNO-MODULATING ACTION

(75) Inventors: Guillaume Lebaut, Saint Sebastien/Loire (FR); Cécilia Menciu, Nantes (FR); Bernhard Kutscher, Maintal (DE); Peter Emig, Bruchköbel (DE); Stefan Szelenyi, Schwaig (DE); Kay Brune, Marloffstein/Rathsberg (DE)

(73) Assignee: Ziopharm Oncology, Inc., Charlestown, MA (US)

Reexamination Request:
No. 90/009,054, Feb. 26, 2008

Reexamination Certificate for:
Patent No.: 6,008,231
Issued: Dec. 28, 1999
Appl. No.: 08/925,326
Filed: Sep. 8, 1997

(*) Notice: This patent is subject to a terminal disclaimer.

Certificate of Correction issued Aug. 28, 2001.

(30) Foreign Application Priority Data
Sep. 6, 1996 (DE) .......................... 196 36 150

(51) Int. Cl.
C07D 401/06 (2006.01)
C07D 209/00 (2006.01)
C07D 209/22 (2006.01)
C07D 401/14 (2006.01)
C07D 401/00 (2006.01)
C07D 401/12 (2006.01)

(52) U.S. Cl. .................. 514/314; 514/339; 514/419; 546/168; 546/278.1; 548/493; 548/491

(58) Field of Classification Search .................. None
See application file for complete search history.

(56) References Cited

U.S. PATENT DOCUMENTS

| | | | |
|---|---|---|---|
| 5,405,864 | A | 4/1995 | Broka |
| 6,008,231 | A | 12/1999 | Lebaut et al. |
| 6,225,329 | B1 | 5/2001 | Richter et al. |
| 6,232,327 | B1 | 5/2001 | Nickel et al. |
| 6,251,923 | B1 | 6/2001 | Hofgen et al. |
| 6,262,044 | B1 | 7/2001 | Moller et al. |
| 6,344,467 | B1 | 2/2002 | Lebaut et al. |
| 6,432,987 | B2 | 8/2002 | Gunther et al. |
| 6,693,119 | B2 | 2/2004 | Nickel et al. |
| 2004/0171668 | A1 | 9/2004 | Nickel et al. |
| 2004/0266762 | A1 | 12/2004 | Gerlach | 
| 2006/0040991 | A1 | 2/2006 | Roessler |
| 2006/0280787 | A1 | 12/2006 | Roessler et al. |

FOREIGN PATENT DOCUMENTS

| | | |
|---|---|---|
| DE | 2 315 989 | 10/1973 |
| DE | 196 361 50 A1 | 3/1998 |
| EP | 1 071 420 B1 | 1/2001 |
| JP | 2000-239252 | 9/2000 |
| WO | WO-98/09946 A1 | 3/1998 |
| WO | WO-99/46237 A1 | 9/1999 |
| WO | WO-99/51224 A1 | 10/1999 |
| WO | WO-99/55696 A1 | 11/1999 |
| WO | WO-00/67802 A1 | 11/2000 |

OTHER PUBLICATIONS

Bacher, et al., "D–24851, a Novel Synthetic Microtubule Inhibitor, Exerts Curative Antitumoral Activity in Vivo, Shows Efficacy toward Multidrug–resistant Tumor Cells, and Lacks Neurotoxicity," Cancer Research, 61(1):392–399 (2001).

Dupont et al., "Antiangiogenic properties of a novel shark cartilage extract: potential role in the treatment of psoriasis," J. Cutan. Med. Surg., 2:146–152 (1998) (Abstract).

Fiszer–Maliszewska et al., "Immunomodulation and Therapeutic Effects of Cytostatics," Zbl. Bakt. Suppl. 13, pp. 215–230 (1985).

Eckhard G. Guenther et al., "Discovery and synthesis of novel N–substituted indolyl–3–glyoxylic acid derivatives with tubulin–binding activity as anti–cancer agents," Proceedings of the American Assoc for Cancer Research Annual Meeting, 41:769 (2000).

Gura, Trisha, "Cancer Models: Systems for Identifying New Drugs Are Often Faulty," Science, 278(5340):1041–1042 (1997).

Johnson et al., British J. of Cancer, 84(10): 1424–1431 (2001).

Ooi Ve, Liu F., Curr. Med. Chem. Jul. 7, 2000(7):715–29, NCBI abstract.

Gerhard Raab et al., "ZIO–301 (Indibulin) a novel tubulin polymerization inhibitor has potent anti–tumor activity and a distinct tubulin binding site," Proceedings of the American Association for Cancer Research Annual Meeting, 48:337 (2007).

Lipp et al., "Some derivatives of 5–benzyloxy–3–indolylgloxylic acid," Chemische Berichte 91:242–243 (1958).

Podwinski, "Synthesis of some 5–benzyloxyindole–3–glyoxylic acid amides," Annales Academiae Medicae Lodzensis 8:153–156 (1966).

Evans et al., "Probing the 5–HT$_3$ receptor site using novel indole–3–glyoxylic acid derivatives," Med Chem Res 3:386–406 (1993).

*Primary Examiner*—Evelyn Huang

(57) ABSTRACT

The invention relates to novel N-substituted indole-3-glyoxylamides, to processes for their preparation and to their pharmaceutical use. The compounds have antiasthmatic, antiallergic and immuno-suppressant/immunomodulating actions.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

New claims 12–14 are added and determined to be patentable.

Claims 2–11 were not reexamined.

1. An N-substituted indol-3-glyoxylamide of formula I:

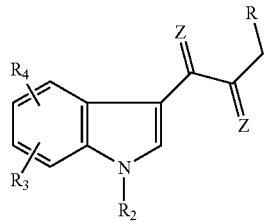

(I)

or an acid addition salt thereof, wherein the radicals R, $R_1$, $R_2$, $R_3$, $R_4$ and Z have the following meanings:

R represents
  (1) hydrogen, or
  (2) $(C_1-C_6)$-alkyl, wherein the alkyl group is optionally mono- or polysubstituted by a phenyl ring,
    which ring is optionally mono- or polysubstituted by halogen, $(C_1-C_6)$-alkyl, $(C_3-C_7)$-cycloalkyl, carboxyl groups, carboxyl groups esterified with $(C_1-C_6)$-alkanols, trifluoromethyl groups, hydroxyl groups, methoxy groups, ethoxy groups, benzyloxy groups and benzyl groups which are optionally mono- or polysubstituted on the phenyl moiety by $(C_1-C_6)$alkyl groups, halogen atoms or trifluoromethyl groups;

$R_1$ represents
  (1) a phenyl ring which is mono- or polysubstituted by $(C_1-C_6)$-alkyl, $(C_1-C_6)$-alkoxy, hydroxyl, benzyloxy, nitro, amino, $(C_1-C_6)$-alkylamino, $(C_1-C_6)$-alkoxy-carbonylamino and by a carboxyl group or a carboxyl group esterified by a $(C_1-C_6)$-alkanol;

(2) a pyridine structure of formula II:

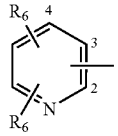

(II)

wherein the pyridine structure is alternatively bonded to the ring carbon atoms 2, 3 and 4 and is optionally substituted by $R_5$ and $R_6$, which may be identical or different and represent $(C_1-C_6)$-alkyl, $(C_3-C_7)$ cycloalkyl, $(C_1-C_6)$alkoxy, nitro, amino, hydroxyl, halogen, trifluoromethyl, an ethoxycarbonylamino radical and a carboxyl alkyloxy group in which the alkyl group has 1–4 carbon atoms;

(3) a pyridylmethyl radical in which $CH_2$ is in the 2-, 3- or 4-position;
  (4) a 2-, 3- or 4-quinolyl structure substituted by $(C_1-C_6)$-alkyl, halogen, a nitro group, an amino group or a $(C_1-C_6)$-alkylamino radical;
  (5) a 2-, 3- or 4-quinolyl methyl group, wherein the ring carbons of the pyridylmethyl and quinolylmethyl radicals are optionally substituted by $(C_1-C_6)$-alkyl, $(C_1-C_6)$-alkoxy, nitro, amino and $(C_1-C_6)$-alkoxycarbonylamino;
  (6) if R represents hydrogen or a benzyl group, $R_1$ can represent the acid radical of a natural amino acid, wherein the amino group of said amino acid is present in protected or unprotected form wherein if $R_1$ represents an asparagyl or a glutamyl radical having a second nonbonded carboxyl group, said nonbonded carboxyl group is present as a free carboxyl group or in the form of an ester with $C_1-C_6$-alkanols;
  (7) an allylaminocarbonyl-2-methylprop-1-yl group;

$R_2$ represents
  [(1) hydrogen;]
  [(2]*1*) a $(C_1-C_6)$-alkyl group,
    said alkyl group being optionally mono- or polysubstituted by halogen or a phenyl ring,
      which ring is optionally mono- or polysubstituted by halogen, $(C_1-C_6)$-alkyl, $(C_3-C_7)$-cycloalkyl, carbonyl groups, carboxyl groups esterified with $(C_1-C_6)$-alkanols, trifluoromethyl groups, hydroxyl groups, methoxy groups, ethoxy groups, or benzyloxy groups;
    or by a 2-quinolyl group or a 2-, 3- or 4-pyridyl structure which are optionally mono- or polysubstituted by halogen, $(C_1-C_4)$-alkyl groups or $(C_1-C_4)$-alkoxy groups;
  ([3]*2*) an aroyl radical, wherein the aroyl moiety on which the radical is based is a phenyl ring which is optionally mono- or polysubstituted by halogen, $(C_1-C_6)$-alkyl, $(C_3-C_7)$-cycloalkyl, carbonyl groups, carboxyl groups esterified with $(C_1-C_6)$-alkanols, trifluoromethyl groups, hydroxyl groups, methoxy groups, ethoxy groups, or benzyloxy groups;

$R_3$ and $R_4$, which are identical or different, represent hydrogen, hydroxyl, $(C_1-C_6)$-alkyl, $(C_3-C_7)$-cycloalkyl, $(C_1-C_6)$-alkanoyl, $(C_1-C_6)$-alkoxy, halogen, benzoxy, a nitro group, an amino group, a $(C_1-C_4)$-mono- or dialkyl substituted amino group, a $(C_1-C_3)$-alkoxycarbonylamino function or a $(C_1-C_3)$-alkoxycarbonylamino-$(C_1-C_3)$-alkyl function; and Z represents O or S;
wherein alkyl, alkanol, alkoxy and alkylamino groups may be straight chained or branched.

12. The N-substituted indol-3-glyoxylamide of claim 1 or an acid addition salt thereof, wherein $R_1$ represents a pyridine structure of formula II:

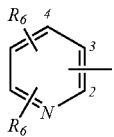

(II)

wherein the pyridine structure is alternatively bonded to the ring carbon atoms 2, 3 and 4 and is optionally substituted by $R_5$ and $R_6$, which may be identical or different and represent $(C_1-C_6)$-alkyl, $(C_3-C_7)$ cycloalkyl, $(C_1-C_6)$alkoxy, nitro, amino, hydroxyl, halogen, trifluromethyl, an ethoxycarbonylamino radical and a carboxyalkyloxy group in which the alkyl group has 1–4 carbon atoms.

13. The N-substituted indol-3-glyoxylamide of claim 1 or an acid addition salt thereof, wherein:

R represents hydrogen;

$R_2$ represents a $(C_1-C_6)$-alkyl group, said alkyl group being substituted by a phenyl ring, which ring is optionally mono- or polysubstituted by halogen, $(C_1-C_6)$-alkyl, $(C_3-C_7)$-cycloalkyl, carbonyl groups, carboxyl groups esterified with $(C_1-C_6)$-alkanols, trifluoromethyl groups, hydroxyl groups, methoxy groups, ethoxy groups, or benzyloxy groups; and $R_3$ and $R_4$ represent hydrogen.

14. The N-substituted indol-3-glyoxylamide of claim 1, wherein the N-substituted indol-3-glyoxylamide is

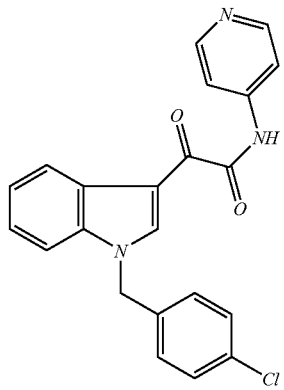

or an acid addition salt thereof.

* * * * *